(12) United States Patent
Handique

(10) Patent No.: US 8,440,149 B2
(45) Date of Patent: *May 14, 2013

(54) HEAT-REDUCTION METHODS AND SYSTEMS RELATED TO MICROFLUIDIC DEVICES

(75) Inventor: Kalyan Handique, Ann Arbor, MI (US)

(73) Assignee: Handylab, Inc., Franklin Lakes, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/367,130

(22) Filed: Feb. 6, 2012

(65) Prior Publication Data

US 2012/0183454 A1 Jul. 19, 2012

Related U.S. Application Data

(63) Continuation of application No. 12/904,432, filed on Oct. 14, 2010, now Pat. No. 8,110,158, which is a continuation of application No. 12/750,471, filed on Mar. 30, 2010, now abandoned, which is a continuation of application No. 12/032,631, filed on Feb. 15, 2008, now abandoned, which is a continuation of application No. 10/778,598, filed on Feb. 17, 2004, now Pat. No. 7,332,130, which is a continuation of application No. 09/783,225, filed on Feb. 14, 2001, now Pat. No. 6,692,700.

(51) Int. Cl.
*B01L 3/00* (2006.01)

(52) U.S. Cl.
USPC ............ 422/504; 422/502; 422/503; 422/547; 422/551

(58) Field of Classification Search ................ 422/68.1, 422/82.01, 502, 503, 504, 547, 551, 552; 436/147, 436/174, 180; 204/400, 424, 435, 436, 451

See application file for complete search history.

(56) References Cited

U.S. PATENT DOCUMENTS

| 1,434,314 A | 10/1922 | Raich |
| 1,616,419 A | 2/1927 | Wilson |

(Continued)

FOREIGN PATENT DOCUMENTS

| CA | 2294819 | 1/1999 |
| DE | 19929734 | 12/1999 |

(Continued)

OTHER PUBLICATIONS

Bollet, C. et al., "A simple method for the isolation of chromosomal DNA from Gram positive or acid-fast bacteria", Nucleic Acids Research, vol. 19, No. 8 (1991), p. 1955.

(Continued)

*Primary Examiner* — Jill Warden
*Assistant Examiner* — Dwayne K Handy
(74) *Attorney, Agent, or Firm* — Knobbe Martens Olson & Bear LLP

(57) ABSTRACT

The present relates to a system and method for preventing or reducing unwanted heat in a microfluidic of the device while generating heat in selected regions of the device. Current can be supplied to a heating element through electric leads that are designed so that the current density in the leads is substantially lower than the current density in the heating element. Unwanted heat in the microfluidic complex can be reduced by thermally isolating the electric leads from the microfluidic complex by, for example, running each lead directly away from the microfluidic complex. Unwanted heat can be removed from selected regions of the microfluidic complex using one or more cooling devices.

29 Claims, 8 Drawing Sheets

U.S. PATENT DOCUMENTS

| | | | |
|---|---|---|---|
| 1,733,401 A | 8/1930 | Lovekin | |
| 3,528,449 A | 9/1970 | Witte et al. | |
| 3,813,316 A | 5/1974 | Chakrabarty et al. | |
| 3,985,649 A | 10/1976 | Eddelman | |
| 4,018,089 A | 4/1977 | Dzula et al. | |
| 4,018,652 A | 4/1977 | Lanham et al. | |
| 4,038,192 A | 7/1977 | Serur | |
| 4,055,395 A | 10/1977 | Honkawa et al. | |
| D249,706 S | 9/1978 | Adamski | |
| 4,139,005 A | 2/1979 | Dickey | |
| D252,157 S | 6/1979 | Kronish et al. | |
| D252,341 S | 7/1979 | Thomas | |
| D254,687 S | 4/1980 | Fadler et al. | |
| 4,212,744 A | 7/1980 | Oota | |
| D261,033 S | 9/1981 | Armbruster | |
| D261,173 S | 10/1981 | Armbruster | |
| 4,301,412 A | 11/1981 | Hill et al. | |
| 4,439,526 A | 3/1984 | Columbus | |
| 4,457,329 A | 7/1984 | Werley et al. | |
| 4,466,740 A | 8/1984 | Kano et al. | |
| 4,504,582 A | 3/1985 | Swann | |
| 4,522,786 A | 6/1985 | Ebersole | |
| D279,817 S | 7/1985 | Chen et al. | |
| 4,599,315 A | 7/1986 | Teraski et al. | |
| 4,612,873 A | 9/1986 | Eberle | |
| 4,612,959 A | 9/1986 | Costello | |
| D288,478 S | 2/1987 | Carlson et al. | |
| 4,654,127 A | 3/1987 | Baker et al. | |
| 4,673,657 A | 6/1987 | Christian | |
| 4,683,195 A | 7/1987 | Mullis et al. | |
| 4,683,202 A | 7/1987 | Mullis | |
| D292,735 S | 11/1987 | Lovborg | |
| 4,720,374 A | 1/1988 | Ramachandran | |
| 4,798,693 A | 1/1989 | Mase et al. | |
| 4,800,022 A | 1/1989 | Leonard | |
| 4,841,786 A | 6/1989 | Schulz | |
| D302,294 S | 7/1989 | Hillman | |
| 4,871,779 A | 10/1989 | Killat et al. | |
| 4,895,650 A | 1/1990 | Wang | |
| 4,919,829 A | 4/1990 | Gates et al. | |
| 4,921,809 A | 5/1990 | Schiff et al. | |
| 4,935,342 A | 6/1990 | Seligson et al. | |
| 4,946,562 A | 8/1990 | Guruswamy | |
| 4,949,742 A | 8/1990 | Rando et al. | |
| D310,413 S | 9/1990 | Bigler et al. | |
| 4,963,498 A | 10/1990 | Hillman | |
| 4,967,950 A | 11/1990 | Legg et al. | |
| 4,978,502 A | 12/1990 | Dole et al. | |
| 4,978,622 A | 12/1990 | Mishell et al. | |
| 4,989,626 A | 2/1991 | Takagi et al. | |
| 5,001,417 A | 3/1991 | Pumphrey et al. | |
| 5,004,583 A | 4/1991 | Guruswamy et al. | |
| 5,048,554 A | 9/1991 | Kremer | |
| 5,053,199 A | 10/1991 | Keiser et al. | |
| 5,060,823 A | 10/1991 | Perlman | |
| 5,061,336 A | 10/1991 | Soane | |
| 5,064,618 A | 11/1991 | Baker et al. | |
| 5,071,531 A | 12/1991 | Soane | |
| 5,091,328 A | 2/1992 | Miller | |
| D324,426 S | 3/1992 | Fan et al. | |
| 5,096,669 A | 3/1992 | Lauks et al. | |
| 5,126,002 A | 6/1992 | Iwata et al. | |
| 5,126,022 A | 6/1992 | Soane et al. | |
| D328,135 S | 7/1992 | Fan et al. | |
| D328,794 S | 8/1992 | Frenkel et al. | |
| 5,135,627 A | 8/1992 | Soane | |
| 5,135,872 A | 8/1992 | Pouletty et al. | |
| 5,147,606 A | 9/1992 | Charlton et al. | |
| 5,169,512 A | 12/1992 | Wiedenmann et al. | |
| D333,522 S | 2/1993 | Gianino | |
| 5,186,339 A | 2/1993 | Heissler | |
| 5,192,507 A | 3/1993 | Taylor et al. | |
| 5,208,163 A | 5/1993 | Charlton et al. | |
| 5,223,226 A | 6/1993 | Whittmer et al. | |
| D338,275 S | 8/1993 | Fischer et al. | |
| 5,250,263 A | 10/1993 | Manz | |
| 5,252,743 A | 10/1993 | Barrett et al. | |
| 5,256,376 A | 10/1993 | Callan et al. | |
| 5,275,787 A | 1/1994 | Yuguchi et al. | |
| 5,282,950 A | 2/1994 | Dietze et al. | |
| 5,296,375 A | 3/1994 | Kricka et al. | |
| 5,304,477 A | 4/1994 | Nagoh et al. | |
| 5,304,487 A | 4/1994 | Wilding et al. | |
| D347,478 S | 5/1994 | Pinkney | |
| 5,311,896 A | 5/1994 | Kaartinen et al. | |
| 5,311,996 A | 5/1994 | Duffy et al. | |
| 5,316,727 A | 5/1994 | Suzuki et al. | |
| 5,327,038 A | 7/1994 | Culp | |
| 5,339,486 A | 8/1994 | Persic, Jr. | |
| D351,475 S | 10/1994 | Gerber | |
| D351,913 S | 10/1994 | Hieb et al. | |
| 5,364,591 A | 11/1994 | Green et al. | |
| 5,372,946 A | 12/1994 | Cusak et al. | |
| 5,374,395 A | 12/1994 | Robinson | |
| 5,389,339 A | 2/1995 | Petschek et al. | |
| 5,397,709 A | 3/1995 | Berndt | |
| 5,401,465 A | 3/1995 | Smethers et al. | |
| 5,411,708 A | 5/1995 | Moscetta et al. | |
| 5,414,245 A | 5/1995 | Hackleman | |
| 5,416,000 A | 5/1995 | Allen et al. | |
| 5,422,271 A | 6/1995 | Chen et al. | |
| 5,422,284 A | 6/1995 | Lau | |
| 5,427,946 A | 6/1995 | Kricka et al. | |
| 5,474,796 A | 12/1995 | Brennan | |
| D366,116 S | 1/1996 | Biskupski | |
| 5,486,335 A | 1/1996 | Wilding et al. | |
| 5,494,639 A | 2/1996 | Grzegorzewski | |
| 5,498,392 A | 3/1996 | Wilding et al. | |
| 5,503,803 A | 4/1996 | Brown | |
| 5,516,410 A | 5/1996 | Schneider et al. | |
| 5,519,635 A | 5/1996 | Miyake et al. | |
| 5,529,677 A | 6/1996 | Schneider et al. | |
| 5,559,432 A | 9/1996 | Logue | |
| 5,565,171 A | 10/1996 | Dovichi et al. | |
| 5,569,364 A | 10/1996 | Hooper et al. | |
| 5,578,270 A | 11/1996 | Reichler et al. | |
| 5,578,818 A | 11/1996 | Kain et al. | |
| 5,579,928 A | 12/1996 | Anukwuem | |
| 5,580,523 A | 12/1996 | Bard | |
| 5,582,884 A | 12/1996 | Ball et al. | |
| 5,585,069 A | 12/1996 | Zanucchi et al. | |
| 5,585,089 A | 12/1996 | Queen et al. | |
| 5,585,242 A | 12/1996 | Bouma et al. | |
| 5,587,128 A | 12/1996 | Wilding et al. | |
| 5,589,136 A | 12/1996 | Northrup et al. | |
| 5,593,838 A | 1/1997 | Zanzucchi et al. | |
| 5,595,708 A | 1/1997 | Berndt | |
| 5,599,432 A | 2/1997 | Manz et al. | |
| 5,599,503 A | 2/1997 | Manz et al. | |
| 5,599,667 A | 2/1997 | Arnold, Jr. et al. | |
| 5,601,727 A | 2/1997 | Bormann et al. | |
| 5,603,351 A | 2/1997 | Cherukuri et al. | |
| 5,605,662 A | 2/1997 | Heller et al. | |
| D378,782 S | 4/1997 | LaBarbera et al. | |
| 5,628,890 A | 5/1997 | Carter et al. | |
| 5,630,920 A | 5/1997 | Friese et al. | |
| 5,631,337 A | 5/1997 | Sassi et al. | |
| 5,632,876 A | 5/1997 | Zanzucchi et al. | |
| 5,632,957 A | 5/1997 | Heller et al. | |
| 5,635,358 A | 6/1997 | Wilding et al. | |
| 5,637,469 A | 6/1997 | Wilding et al. | |
| 5,639,423 A | 6/1997 | Northrup et al. | |
| 5,643,738 A | 7/1997 | Zanzucchi et al. | |
| 5,646,039 A | 7/1997 | Northrup et al. | |
| 5,647,994 A | 7/1997 | Tuunanen et al. | |
| 5,651,839 A | 7/1997 | Rauf | |
| 5,652,149 A | 7/1997 | Mileaf et al. | |
| D382,346 S | 8/1997 | Buhler et al. | |
| D382,647 S | 8/1997 | Staples et al. | |
| 5,667,976 A | 9/1997 | Van Ness et al. | |
| 5,671,303 A | 9/1997 | Shieh et al. | |
| 5,674,394 A | 10/1997 | Whitmore | |
| 5,674,742 A | 10/1997 | Northrup et al. | |
| 5,681,484 A | 10/1997 | Zanzucchi et al. | |
| 5,681,529 A | 10/1997 | Taguchi et al. | |
| 5,683,657 A | 11/1997 | Mian | |
| 5,699,157 A | 12/1997 | Parce | |

| Patent | Date | Inventor |
|---|---|---|
| 5,700,637 A | 12/1997 | Southern |
| 5,705,813 A | 1/1998 | Apffel et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benregnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| D438,632 S | 3/2001 | Miller |
| D438,633 S | 3/2001 | Miller |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |

| Patent No. | Date | Inventor |
|---|---|---|
| 6,236,581 B1 | 5/2001 | Foss et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,287,254 B1 | 9/2001 | Dodds |
| 6,287,774 B1 | 9/2001 | Kikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher et al. |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | McCormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,620,625 B2 | 9/2003 | Wolk et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,649,358 B1 | 11/2003 | Parce et al. |
| D484,989 S | 1/2004 | Gebrian |
| 6,681,616 B2 | 1/2004 | Spaid et al. |
| 6,692,700 B2 | 2/2004 | Handique |
| 6,706,519 B1 | 3/2004 | Kellogg et al. |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,752,966 B1 | 6/2004 | Chazan |
| 6,756,019 B1 | 6/2004 | Dubrow et al. |
| 6,773,567 B1 | 8/2004 | Wolk |
| 6,783,962 B1 | 8/2004 | Olander et al. |
| D495,805 S | 9/2004 | Lea et al. |
| 6,790,328 B2 | 9/2004 | Jacobson et al. |
| 6,811,668 B1 | 11/2004 | Berndt et al. |
| 6,818,113 B2 | 11/2004 | Williams et al. |
| 6,824,663 B1 | 11/2004 | Boone |
| D499,813 S | 12/2004 | Wu |
| D500,142 S | 12/2004 | Crisanti et al. |
| 6,827,831 B1 | 12/2004 | Chow et al. |
| 6,827,906 B1 | 12/2004 | Bjornson et al. |
| 6,852,287 B2 | 2/2005 | Ganesan |
| 6,858,185 B1 | 2/2005 | Kopf-sill et al. |
| 6,878,540 B2 | 4/2005 | Pourahmadi et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,942,771 B1 | 9/2005 | Kayyem |
| 7,024,281 B1 | 4/2006 | Unno |
| 7,037,416 B2 | 5/2006 | Parce et al. |
| 7,039,527 B2 | 5/2006 | Tripathi et al. |
| 7,138,032 B2 | 11/2006 | Gandhi et al. |
| 7,169,618 B2 | 1/2007 | Skold |
| 7,192,557 B2 | 3/2007 | Wu et al. |
| 7,235,406 B1 | 6/2007 | Woudenberg et al. |
| 7,270,786 B2 | 9/2007 | Parunak et al. |
| 7,323,140 B2 | 1/2008 | Handique et al. |
| 7,332,130 B2 | 2/2008 | Handique |

| Patent/Publication No. | Date | Name |
|---|---|---|
| 7,338,760 B2 | 3/2008 | Gong et al. |
| 7,374,949 B2 | 5/2008 | Kuriger |
| 7,390,460 B2 | 6/2008 | Osawa et al. |
| 7,476,313 B2 | 1/2009 | Siddiqi |
| 7,494,770 B2 | 2/2009 | Wilding et al. |
| 7,553,671 B2 | 6/2009 | Sinclair et al. |
| 7,604,938 B2 | 10/2009 | Takahashi et al. |
| 7,674,431 B2 | 3/2010 | Ganesan |
| 7,704,735 B2 | 4/2010 | Facer et al. |
| 7,744,817 B2 | 6/2010 | Bui |
| 7,998,708 B2 | 8/2011 | Handique et al. |
| 8,088,616 B2 | 1/2012 | Handique |
| 8,105,783 B2 | 1/2012 | Handique |
| 8,133,671 B2 | 3/2012 | Williams et al. |
| 8,182,763 B2 | 5/2012 | Duffy et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0049833 A1 | 3/2003 | Chen et al. |
| 2003/0064507 A1 | 4/2003 | Gallagher et al. |
| 2003/0070677 A1 | 4/2003 | Handique et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0199081 A1 | 10/2003 | Wilding et al. |
| 2003/0211517 A1 | 11/2003 | Carulli et al. |
| 2004/0014238 A1 | 1/2004 | Krug et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0086956 A1 | 5/2004 | Bachur, Jr. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0240097 A1 | 12/2004 | Evans |
| 2005/0009174 A1 | 1/2005 | Nikiforov et al. |
| 2005/0041525 A1 | 2/2005 | Pugia et al. |
| 2005/0048540 A1 | 3/2005 | Inami et al. |
| 2005/0058574 A1 | 3/2005 | Bysouth et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0133370 A1 | 6/2005 | Park et al. |
| 2005/0135655 A1 | 6/2005 | Kopf-sill et al. |
| 2005/0152808 A1 | 7/2005 | Ganesan |
| 2005/0170362 A1 | 8/2005 | Wada et al. |
| 2005/0186585 A1 | 8/2005 | Juncosa et al. |
| 2005/0202470 A1 | 9/2005 | Sundberg et al. |
| 2005/0202504 A1 | 9/2005 | Anderson et al. |
| 2005/0208676 A1 | 9/2005 | Kahatt |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0207944 A1 | 9/2006 | Siddiqi |
| 2006/0246493 A1 | 11/2006 | Jensen et al. |
| 2006/0246533 A1 | 11/2006 | Fathollahi et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0026421 A1 | 2/2007 | Sundberg et al. |
| 2007/0042441 A1 | 2/2007 | Masters et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0050804 A1 | 2/2008 | Handique et al. |
| 2008/0056948 A1 | 3/2008 | Dale et al. |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0182301 A1 | 7/2008 | Handique et al. |
| 2008/0192254 A1 | 8/2008 | Kim et al. |
| 2008/0247914 A1 | 10/2008 | Edens et al. |
| 2008/0262213 A1 | 10/2008 | Wu et al. |
| 2009/0047713 A1 | 2/2009 | Handique |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0189089 A1 | 7/2009 | Bedingham et al. |
| 2009/0221059 A1 | 9/2009 | Williams et al. |

| | | | |
|---|---|---|---|
| 2009/0223925 | A1 | 9/2009 | Morse et al. |
| 2010/0009351 | A1 | 1/2010 | Brahmasandra et al. |
| 2012/0171759 | A1 | 7/2012 | Williams et al. |
| 2012/0258463 | A1 | 10/2012 | Duffy et al. |

FOREIGN PATENT DOCUMENTS

| | | |
|---|---|---|
| EP | 0766256 | 4/1997 |
| FR | 2672301 | 8/1992 |
| FR | 2795426 | 12/2000 |
| JP | 58212921 A | 12/1983 |
| JP | 07-290706 | 11/1995 |
| JP | 2001-502790 | 1/1998 |
| JP | 2000-514928 | 4/1999 |
| JP | 2001-509437 | 7/2001 |
| JP | 2001-515216 | 9/2001 |
| JP | 2001-527220 | 12/2001 |
| JP | 2002-215241 | 7/2002 |
| JP | 2003-500674 | 1/2003 |
| JP | 2005-514718 | 5/2005 |
| JP | 2005-204661 | 8/2005 |
| JP | 2005-291954 A | 10/2005 |
| WO | WO 88/06633 | 9/1988 |
| WO | WO 90/12350 | 10/1990 |
| WO | WO 92/05443 | 4/1992 |
| WO | WO 97/05492 | 2/1997 |
| WO | WO 98/00231 | 1/1998 |
| WO | WO 98/22625 | 5/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/072264 | 9/2002 |
| WO | WO 02/078845 | 10/2002 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 2004/007081 | 1/2004 |
| WO | WO 2004/074848 | 9/2004 |
| WO | WO 2005/011867 | 2/2005 |
| WO | WO 2005/108620 | 11/2005 |
| WO | WO 2006/079082 | 7/2006 |
| WO | WO 2007/050327 | 5/2007 |
| WO | WO 2008/030914 | 3/2008 |
| WO | WO 2008/060604 | 5/2008 |
| WO | WO 2009/012185 | 1/2009 |
| WO | WO 2010/118541 | 10/2010 |

OTHER PUBLICATIONS

Brahmassandra, et al., On-Chip DNA Detection in Microfabricated Separation Systems, Part of the SPIE Conference on Microfludic Devices and Systems, 1998, Santa Clara, California, vol. 3515, pp. 242-251.

Brody, et al., Diffusion-Based Extraction in a Microfabricated Device, Sensors and Actuators Elsevier, 1997, vol. A58, No. 1, pp. 13-18.

Broyles, et al., "Sample Filtration, Concentration, and Separation Integrated on Microfluidic Devices" Analytical Chemistry (American Chemical Society), vol. 75 No. 11: pp. 2761-2767.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, p. 381-385, Miyazaki, Japan, Jan. 2000.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Micochannel", J. Micromech. Microeng., 11:548-554 (2001).

Handique, K. et al., "Nanoliter Liquid Metering in Microchannels Using Hydrophobic Patterns", Anal. Chem., 72:4100-4109 (2000).

He, et al., Microfabricated Filters for Microfludic Analytical Systems, Analytical Chemistry, American Chemical Society, 1999, vol. 71, No. 7, pp. 1464-1468.

Ibrahim, et al., Real-Time Microchip PCR for Detecting Single-Base DIfferences in Viral and Human DNA, Analytical Chemistry, American Chemical Society, 1998, vol. 70, No. 9, pp. 2013-2017.

Khandurina, et al., Microfabricated Porous Membrane Structure for Sample Concentraction and Electrophoretic Analysis, Analytical Chemistry American Chemical Society, 1999, vol. 71, No. 9, pp. 1815-1819.

Kopp, et al., Chemical Amplification: Continuous-Flow PCR on a Chip, www.sciencemag.org, 1998, vol. 280, pp. 1046-1048.

Kutter, et al., Solid Phase Extraction on Microfludic Devices, J. Microcolumn Separations, John Wiley & Sons, Inc., 2000, vol. 12, No. 2, pp. 93-97.

Lagally, et al., Single-Molecule DNA Amplification and Analysis in an Integrated Microfluidic Device, Analytical Chemistry, American Chemical Society, 2001, vol. 73, No. 3 pp. 565-570.

Livache, T. et al., "Polypyrrole DNA chip on a Silicon Device: Example of Hepatitis C Virus Genotyping", Analytical Biochemistry, vol. 255 (1998), pp. 188-194.

Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk, et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.

Ross, et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, et al., Chip PCR.I. Surface Passivation of Microfabricated Silicon-Glass Chips for PCR, Nucleic Acids Research, Oxford University Press, 1996, vol. 24, No. 2, 375-379.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

Mascini et al., "DNA electrochemical biosensors", Fresenius J. Anal. Chem., 369: 15-22, (2001).

Plambeck et al., "Electrochemical Studies of Antitumor Antibiotics", J. Electrochem Soc.: Electrochemical Science and Technology (1984), 131(11): 2556-2563.

Wang, "Survey and Summary, from DNA Biosensors to Gene Chips", Nucleic Acids Research, 28(16):3011-3016, (2000).

Yoza et al., DNA extraction using bacterial magnetic particles modified with hyperbranched polyamidoamine dendrimer, Mar. 20, 2003, vol. 101, No. 3, 219-228.

*Fig. 2*
*(Prior Art)*
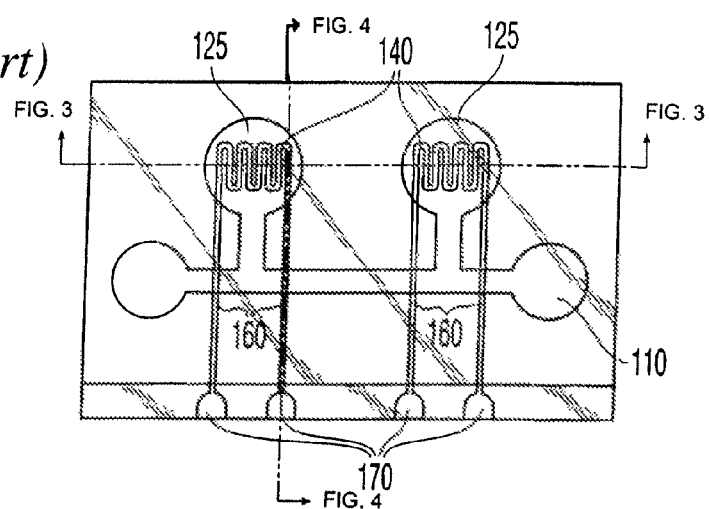
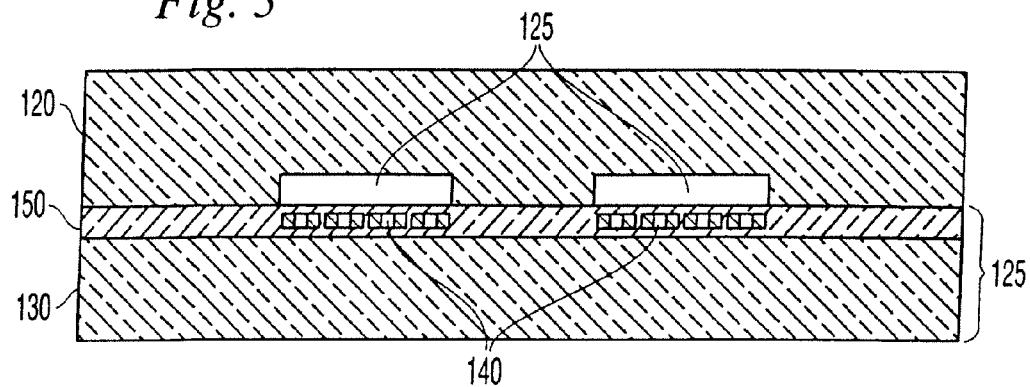
*Fig. 3*
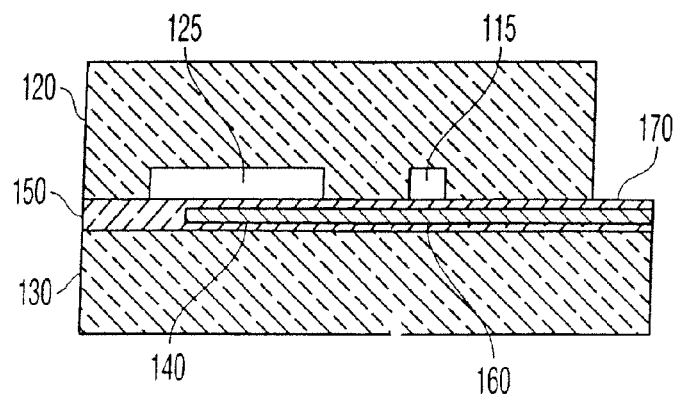
*Fig. 4*

*Fig. 13*
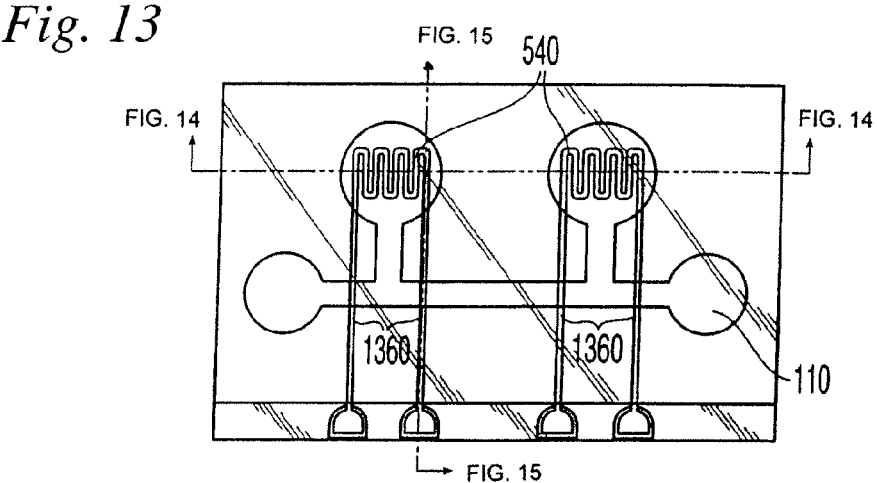
*Fig. 14*
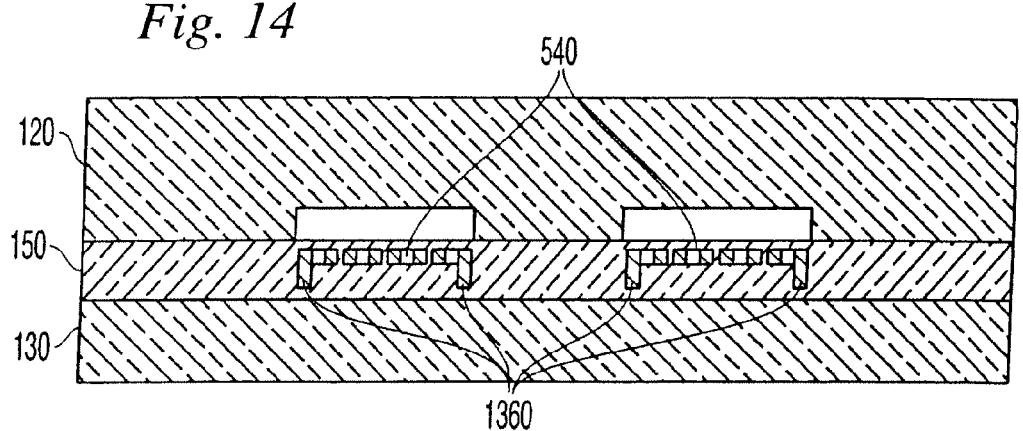
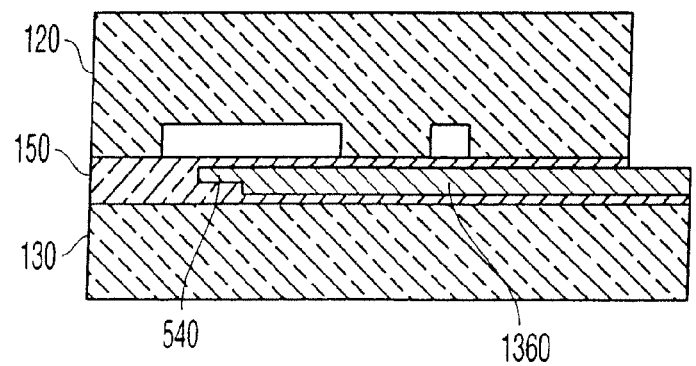
*Fig. 15*

HEAT-REDUCTION METHODS AND SYSTEMS RELATED TO MICROFLUIDIC DEVICES

CROSS-REFERENCE TO RELATED APPLICATIONS

This application is a continuation of U.S. application Ser. No. 12/904,432, filed Oct. 14, 2010, now U.S. Pat. No. 8,110,158, which is a continuation of U.S. application Ser. No. 12/750,471, filed Mar. 30, 2010 now abandoned, which is a continuation of U.S. application Ser. No. 12/032,631, filed Feb. 15, 2008 now abandoned, which is a continuation of U.S. application Ser. No. 10/778,598, filed Feb. 17, 2004, now U.S. Pat. No. 7,332,130, which is a continuation of U.S. application Ser. No. 09/783,225, filed Feb. 14, 2001, now U.S. Pat. No. 6,692,700, the entire contents of all of which are hereby incorporated by reference.

BACKGROUND OF THE INVENTION

1. Field of the Invention

The present invention relates to microfluidic devices, and more particularly to heat management in such devices.

2. Description of the Related Art

Microfluidic devices are known. For example, U.S. Pat. No. 6,130,098 ("the '098 patent") (the contents of which are incorporated herein in their entirety by reference) discloses microfluidic devices that include microdroplet channels for transporting fluid droplets through a fluid processing system. The system includes a variety of microscale components for processing the fluid droplets, including micro-reaction chambers, electrophoresis modules, and detectors (such as radiation detectors). In some embodiments, the devices also include air chambers to internally generate air pressure to automatically withdraw a measured volume of fluid from an input port.

Typically, these elements are microfabricated from silicon, glass, ceramic, plastic, and/or quartz substrates. The various fluid-processing components are linked by microchannels, through which the fluid droplets flow under the control of a fluid propulsion mechanism. If the substrate is formed from silicon, electronic components may be fabricated on the same substrate, allowing sensors and controlling circuitry to be incorporated in the same device. Since all of the components are made using conventional photolithographic techniques, multi-component devices can be readily assembled into complex, integrated systems.

Microfluidic devices use heating elements to accomplish a variety of tasks. For example, U.S. Pat. No. 6,130,098 discloses devices that use heating elements to automatically withdraw a measured volume of fluid from a fluid input port. Liquid placed into a fluid port flows into a channel, past a chamber connected to the side of the channel, and stops at a hydrophobic patch on the wall of the channel. The chamber is then heated, causing pressure to build up. Once the pressure reaches a particular threshold, a microdroplet splits from the rest of the liquid, and is pushed over the hydrophobic patch and down the channel for further processing.

Heating elements can also be used to move such a measured microfluidic droplet through an etched channel. This can be accomplished using a heat-controlled pressure chamber as described in the '098 patent. Fluid movement can also be performed using a series of heaters to generate thermal gradients to change the interfacial tension at the front or back of the droplets, thereby generating a pressure difference across the droplet. For example, a droplet can be propelled forward by heating the back interface. The local increase in temperature reduces the surface tension on the back surface of the droplet and decreases the interfacial pressure difference. The decreased pressure difference corresponds to an increase in the local internal pressure on that end of the droplet. The two droplet interfaces (front and back) are no longer in equilibrium, and the pressure difference propels the droplet forward. Forward motion can be maintained by continuing to heat the droplet at the rear surface with successive heaters along the channel (see FIG. 5 of U.S. Pat. No. 6,130,098), while heating the opposite surface can be used to reverse the motion of the droplet.

Other heater elements may be used to control the temperature in reaction chambers, for example, to perform PCR. Others may be used to manipulate valves made of meltable material (such as wax or solder) as described in U.S. Pat. No. 6,048,734.

All such heater elements, when heating a particular region of a microfluidic device, tend to generate unwanted heat in other regions of the device. Such unwanted heat may adversely affect operation of the microfluidic devices. For example, too much heat can adversely affect the properties of a liquid or gas being processed.

SUMMARY OF THE INVENTION

The invention relates to a system and method for preventing or reducing unwanted heat in a microfluidic device while generating heat in selected regions of the device.

In one aspect, the invention involves supplying current to a heating element through electric leads, wherein the leads are designed so that the current density in the leads is substantially lower than the current density in the heating element. In a preferred embodiment, this is accomplished using conductive leads which have a cross-sectional area which is substantially greater than the cross-sectional area of the heating element.

In another aspect, the invention involves reducing the amount of unwanted heat in the microfluidic complex by thermally isolating the electric leads from the microfluidic complex. In a preferred embodiment, this is accomplished by running each lead directly away from the microfluidic complex, through a thermally isolating substrate. After passing through the thermally isolating substrate, the leads are then routed to the current source. Thus, the thermally isolating substrate substantially blocks the transfer of heat from the leads to the microfluidic complex.

In another aspect, the invention involves removing unwanted heat from selected regions of the microfluidic complex using one or more cooling devices. In a preferred embodiment, one or more Peltier cooling devices are attached to a substrate to remove heat generated by heating elements and/or other electronic circuitry.

BRIEF DESCRIPTION OF THE DRAWINGS

FIG. 2 shows a top-down view of the device in FIG. 1, assembled.

FIG. 3 shows a cross-sectional end view of the device in FIG. 2.

FIG. 4 shows a cross-sectional side view of the device in FIG. 2.

FIG. 13 depicts a top-down view of a device comprising a further preferred embodiment of the present invention.

FIG. 14 depicts a cross-sectional end view of the device in FIG. 13.

FIG. 15 depicts a cross-sectional side view of the device in FIG. 13.

DETAILED DESCRIPTION OF PREFERRED EMBODIMENTS

The present invention relates to microfluidic devices, and in particular, heat management in such devices.

Microfluidic devices typically include micromachined fluid networks in an integrated analysis system. Fluid samples and reagents are brought into the device through entry ports and transported through channels to a reaction chamber, such as a thermally controlled reactor where mixing and reactions (e.g., restriction enzyme digestion or nucleic acid amplification) occur. The biochemical products may then be moved, for example, to an electrophoresis module, where migration data is collected by a detector and transmitted to a recording instrument. The fluidic and electronic components are preferably designed to be fully compatible in function and construction with the biological reactions and reagents.

Figure 1:
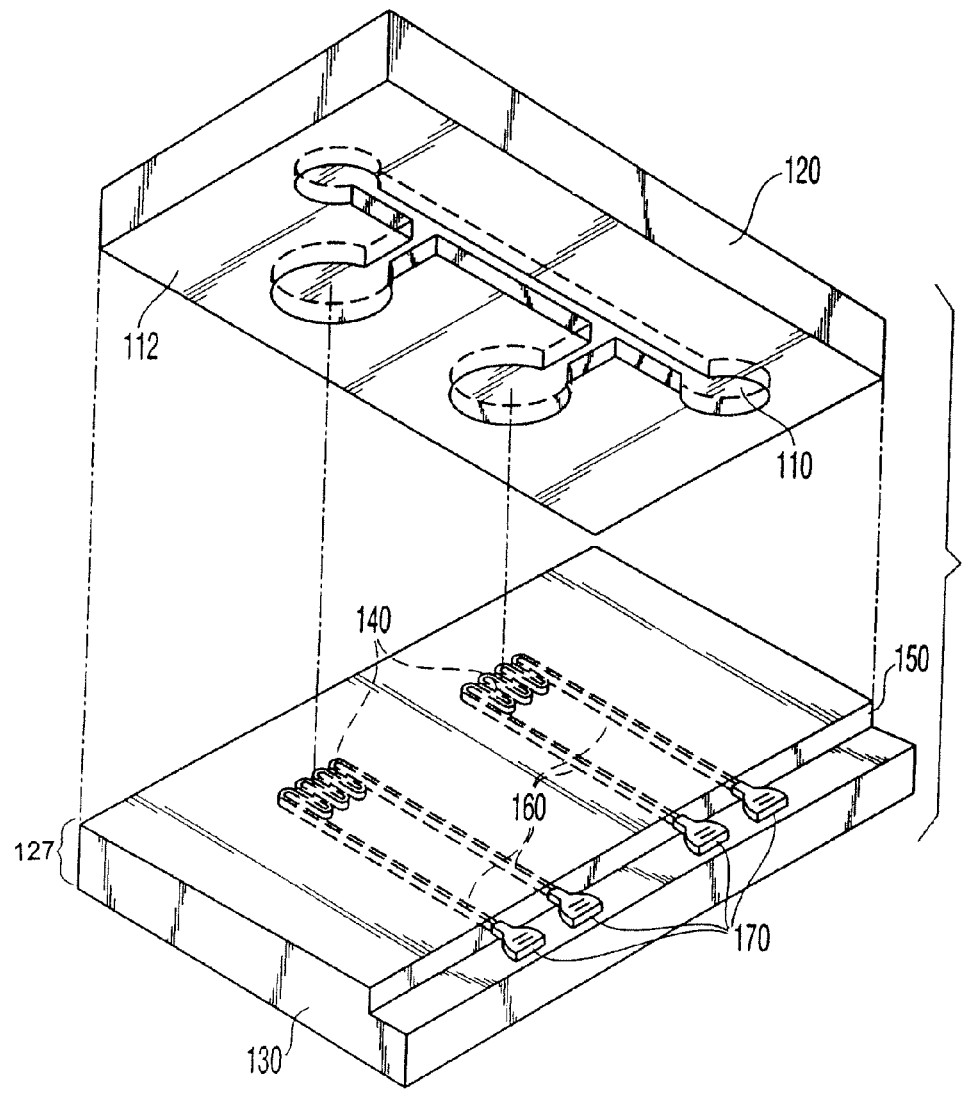
FIG. 1 is an expanded view of a microfluidic device as is known in the art.

There are many formats, materials, and size scales for constructing such integrated micro-fluidic systems. FIG. 1 shows an expanded view of a simple microfluidic device, which will be used to illustrate some of the heat management techniques of the present invention. The device includes an upper substrate 120, which is bonded to a lower substrate 127 to form a fluid network (see FIGS. 2-4).

The upper substrate 120 depicted in FIG. 1 is preferably formed of glass and has a microfluidic complex 110 in its bottom surface 112. Those skilled in the art will recognize that substrates composed of silicon, glass, ceramics, plastic, and/or quartz are all acceptable in the context of the present invention.

Microfluidic complex 110 includes a plurality of chambers connected by a network of microchannels. The number of chambers and channels, as well as the overall topology of the microfluidic complex, will depend upon the particular application which the microfluidic device is designed to perform. However, FIG. 1 depicts a simple microfluidic complex for purposes of illustrating the heat management techniques of the present invention, and is not intended to depict a microfluidic complex for any particular application.

The channels and chambers of the microfluidic complex are etched in the bottom surface 112 of the glass substrate 120 using known photolithographic techniques. More specifically, transparent templates or masks containing opaque designs are used to photo-define objects on the surface of the substrate. The patterns on the templates are generated with computer-aided-design programs and can delineate structures with line-widths of less than one micron. Once a template is generated, it can be used almost indefinitely to produce identical replicate structures. Consequently, even extremely complex microfluidic complexes can be reproduced in mass quantities and at low incremental unit cost.

The lower substrate 127 includes a glass base 130 and an oxide layer 150. Within oxide layer 150, resistive heaters 140 and electric leads 160 are formed. The leads 160 connect to terminals 170 which are exposed at the edge of the substrate to permit electrical connection to an external voltage source (not shown) that controls the heaters. More specifically, to activate a heater 140, a voltage is applied across a pair of terminals 170 to supply current through leads 160 and heater 140, thereby heating the resistive heater element 140. However, since the same current passes through leads 160, these leads are also heated.

Metal heater elements 140 are positioned so that, when the upper and lower substrates are bonded together, the heaters reside directly beneath the fluid chambers of the upper substrate so as to be able to heat the contents of the microchambers. The silicon oxide layer 150 prevents the heating elements 140 from directly contacting with fluid in the microfluidic complex 110.

The oxide layer 150, heating elements 140, and resistive leads 160 are fabricated using well-known photolithographic techniques, such as those used to etch microfluidic complex 110.

FIG. 2 is a top-down view of the device in FIG. 1. In this figure, upper substrate 120 is shown atop substrate 127 and silicon oxide layer 150. Each microchamber 125 of the microfluidic complex is directly above a corresponding heater element 140 to allow the heater to raise the temperature of the contents of the chamber. (This relationship is shown more clearly in the cross-sectional end view of the device depicted in FIG. 3).

However, as shown in FIG. 2, the leads 160 (which supply current to the heaters) pass directly beneath microchannel 115. This relationship is more clearly shown in cross-sectional side view of the device depicted in FIG. 4.

FIG. 4 clearly shows the leads 160 positioned beneath microchannel 115 and separated from the channel 115 by only a thin layer of oxide. Thus, the leads 160, when carrying current to heater 140, may warm any fluid (or gas or meltable material) in the microchannel 115, thereby possibly adversely affecting the operation of the microfluidic device.

Referring again to FIG. 2, the heater leads 160 also run close to the channels connecting chambers 125 to channel 115. Accordingly, when the leads are supplying electric current to heater 140, they may also unintentionally warm the contents of any fluid or wax in the side channels.

Figure 5:
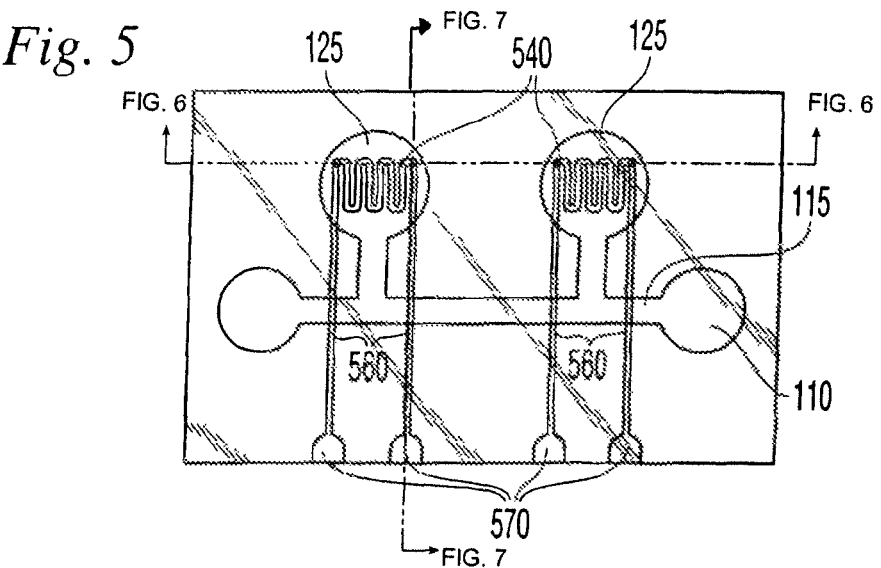
FIG. 5 shows a top-down view of a device comprising a preferred embodiment of the present invention.
Figure 6:
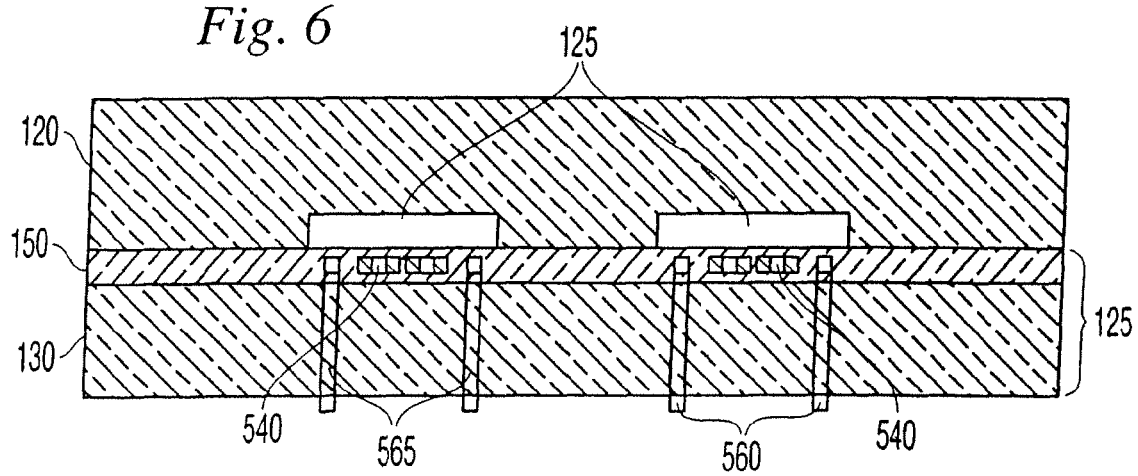
FIG. 6 shows a cross-sectional end view of the device in FIG. 5.
Figure 7:
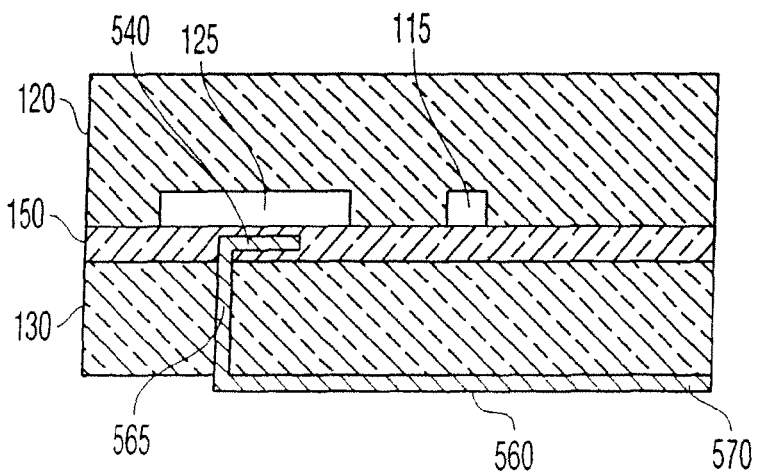
FIG. 7 shows a cross-sectional side view of the device in FIG. 5.
Figure 8:
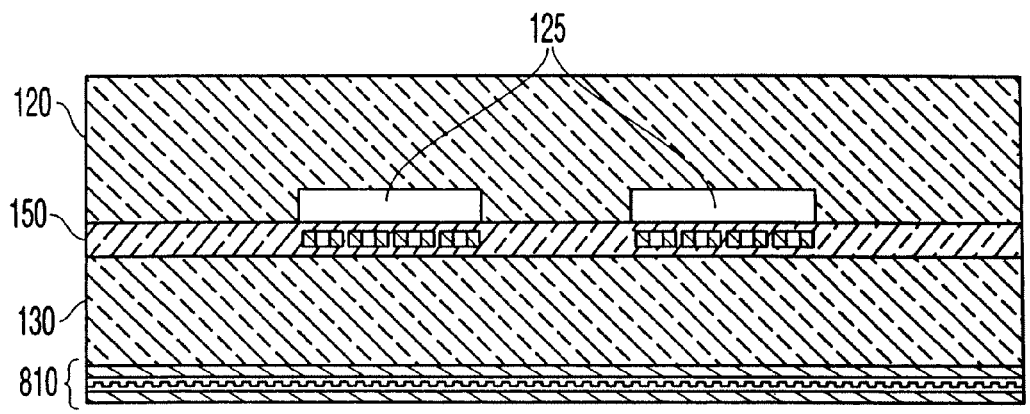
FIG. 8 depicts the device in FIG. 3, with a Peltier device attached to the lower substrate.
Figure 9:
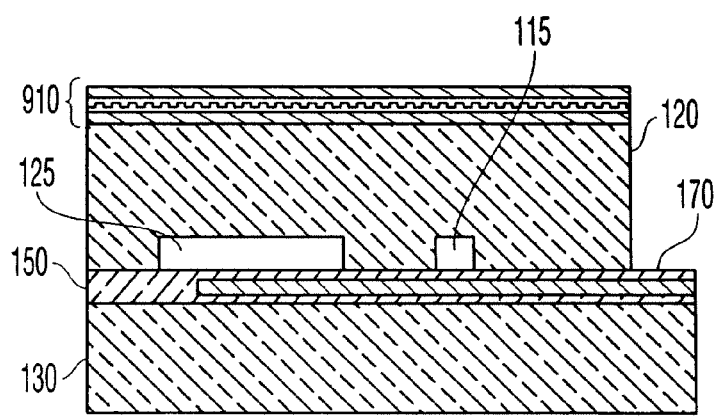
FIG. 9 depicts the device in FIG. 4, with a Peltier device attached to the upper substrate.

FIGS. 5-7 depict the structure of a first preferred embodiment of the invention which eliminates, or at least substantially reduces, such unwanted heat from the leads. In this structure, the resistive heating elements 540 reside in the oxide layer directly beneath chamber 125, just as they do in the structure shown in FIG. 2. However, unlike the structure of FIG. 2, the electrical leads do NOT reside in the oxide layer 150. Rather, as shown in FIG. 6, the leads 565 first pass directly through the oxide layer 150 and glass base 130 to the opposite side of the substrate 130 (herein "vertical leads"). Preferably the vertical leads 565 are orthogonal to the plane in which heater elements 540 reside.

The vertical leads 565 are then connected to horizontal leads 560, which run along the opposite side of substrate 130 and connect to terminals 570 as shown in FIG. 7. Also as shown in FIG. 7, horizontal leads 560 run under channel 115. However, they are now separated from the channel by the full oxide layer 150 and base 130 which act as a thermal isolating layer. Base 130 and oxide 150 should collectively have a sufficiently low thermal conductivity to substantially prevent heat emitted by the leads on the bottom of substrate 130 from adversely affecting the operation of the microfluidic complex 110. Thus, this configuration substantially reduces the amount of heat transmitted from the leads 560 to the microfluidic complex 110.

Those skilled in the art will recognize that the above described technique is not limited to microfluidic devices formed from a pair of substrates, such as shown in Fig. Rather, the technique is generally useful in microfluidic devices for reducing unwanted transfer of heat generated by the electric leads. Regardless of how the microfluidic complex is formed, unwanted heat transfer is reduced if the electric leads are routed from the terminals of the heating element through a thermally resistive material, such that the leads are substantially isolated from the microfluidic complex.

The vertical leads shown in FIGS. 5 and 6 may be formed by drilling holes through substrate 130 before oxide layer 150 and heater 540 are formed. Typically, such holes are 200-500 µm in diameter, but it should be understood that the size of or method of constructing the hole may vary. Preferred means for drilling the holes are related to the desired diameter. For holes 300 µm and greater, mechanical drilling or ultrasonic drilling is preferred, although laser drilling also works. Laser drilling presently works for holes as small as 200 µm in diameter; recent research indicates that laser drilling may also work for holes as small as 50 µm in diameter, or smaller.

Leads 565 may be run through the holes either by electroplating or by squeezing conductive materials (e.g., pastes) through the holes using screen-printing techniques. Materials for electroplating include aluminum, gold, and nickel, as known in the art. Materials for conductive paste include silver-filled epoxy, although other pastes are known to those skilled in the art to be appropriate.

Figure 17:
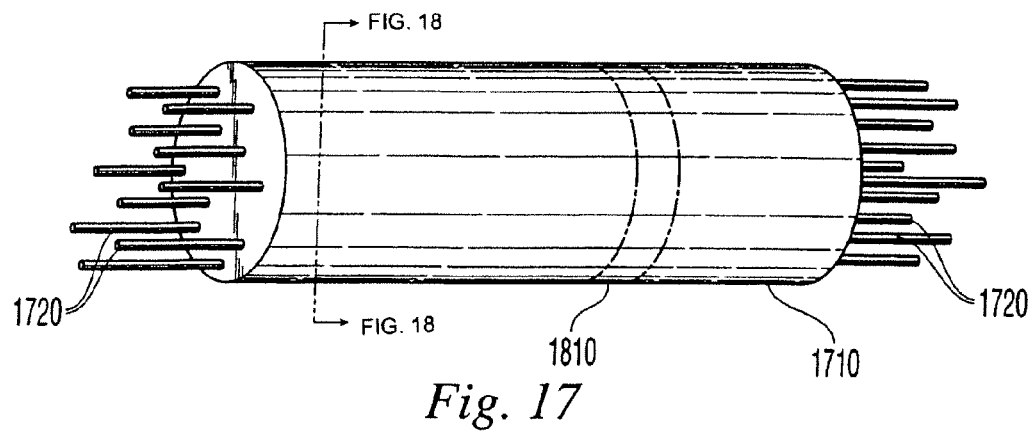
FIG. 17 depicts a cylinder of substrate material comprising wires that run parallel to the axis of the cylinder and that are spaced cross-sectionally as the vertical leads are desired to be spaced in the substrate.
Figure 18:
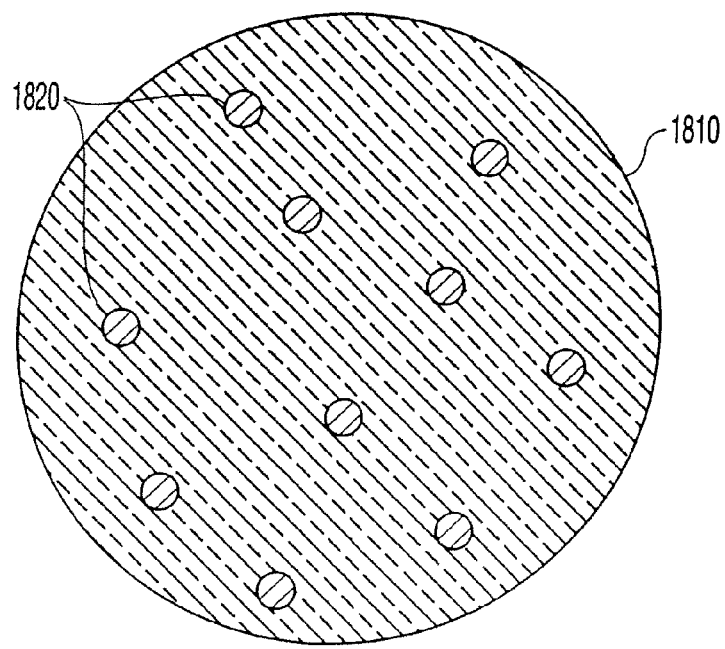
FIG. 18 depicts a lead-gridded substrate formed by slicing the cylinder depicted in FIG. 17 into a cross-section of the desired thickness.

An alternative method of creating the vertical leads 565 is to form a substrate that comprises a "grid" of vertical leads, such as shown in FIG. 18. Referring to FIG. 17, such a "lead-gridded" substrate 1810 is preferably fabricated by stretching a plurality of wires through a tabular shaped mold 1710, with the wires spaced in the same spacing desired for the intended leads. (Alternatively, the leads can be laid out in a rectangular matrix, for example, and the heater leads run to the nearest pair of vertical leads). Then, a substrate material (such as plastic) is injected into the tube 1710 (or an elongated quadrilateral or another shape appropriate to the method described herein) and surrounds the wires 1720. The result is a cylinder of substrate material comprising wires 1720 that run parallel to the axis of the tube and that are spaced cross-sectionally as the vertical leads are desired to be spaced in the substrate. See FIG. 17. Then, to obtain a lead-gridded substrate, the remaining steps are to slice the cylinder into a cross-section 1810 of the desired thickness and polish as necessary. See FIG. 18. Those skilled in the art will recognize the cost efficiency of this method, in that multiple lead-gridded substrates (of uniform or varying thicknesses) can be obtained from a single wired cylinder of the type shown in FIG. 17.

Referring to FIGS. 13-15, unwanted heat transfer from the leads to a microfluidic complex 110 may also be reduced by substantially decreasing the current density in the leads relative to the current density in the heating elements. In the structure shown in FIGS. 13-15, this is accomplished by providing the leads with a greater thickness than the conductors of the heater element 540. For example, as shown in FIGS. 14,15, the leads 1360 are substantially thicker than the conductor which forms the heating element 540. Increasing the vertical thickness of the lead wires increases the cross-sectional area of the lead wires, thus decreasing the electrical resistance of the wires. This also decreases the current density within the leads and thereby decreases the amount of heat radiated by the leads when a given current is applied.

Figure 16:
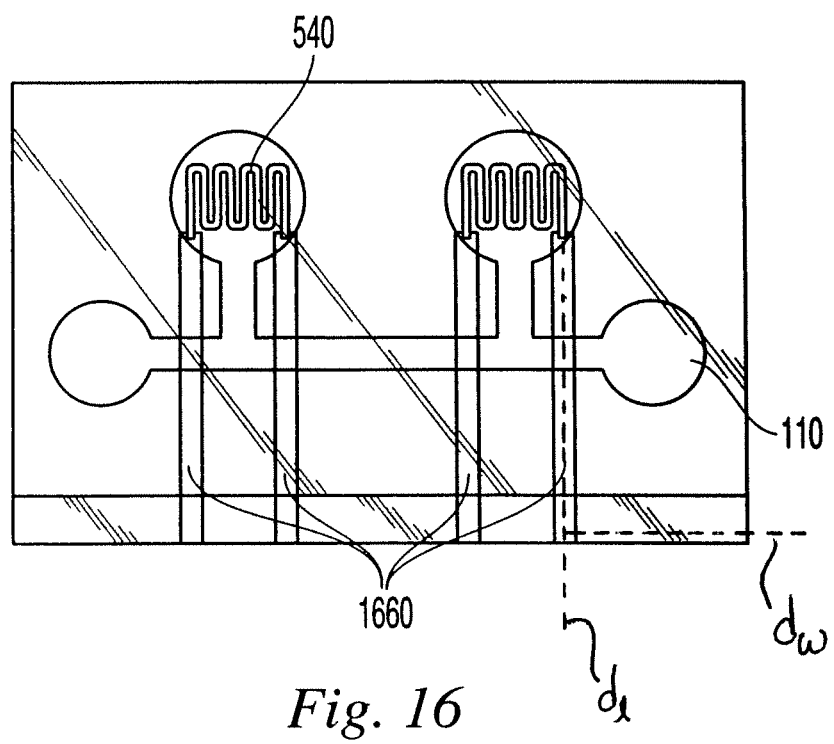
FIG. 16 depicts a top-down view of a device comprising a further preferred embodiment of the present invention.

Referring to FIG. 16, heat transfer from the leads to a microfluidic complex 110 may also be reduced by increasing the horizontal thickness of the electric leads 1660 that connect heater elements 540 to a power source. Here, "horizontal" means in a direction parallel to the plane in which oxide layer 150 lies (refer to FIG. 15, for example). The leads 1660 have a length taken along a dimension $d_l$, which is parallel to the plane in which oxide layer 150 lies. Leads 1660 are thicker than heater element 540 along a dimension $d_w$, which is parallel to the plane in which oxide layer 150 lies and orthogonal to dimension $d_l$, of the leads. The preferred configuration is similar to that shown in FIGS. 2-4. However, the improvement comprised in the embodiment shown in FIG. 16 lies in the increased horizontal thickness of leads 1660. Increasing the horizontal thickness of the leads increases the cross-sectional area of the lead wires, thus decreasing the electrical resistance of the wires. This in turn decreases the amount of heat radiated by the wires when a given current is applied, thus decreasing the amount of heat transferred from the wires to microfluidic complex 110.

An advantage of increasing the horizontal thickness instead of the vertical thickness is that there is less likely to be a need to increase the thickness of the oxide layer 150. On the other hand, an advantage of increasing the vertical thickness instead of the horizontal thickness is that a greater number of leads can be used on the substrate without interfering with each other.

In a still further embodiment, the thickness of the leads is increased in both the horizontal and vertical directions. Those skilled in the art will recognize that the leads can be modified in a variety of ways without departing from the scope of the invention, as long as it results in a substantial decrease in the current density within the leads (relative to the current density in the heating elements) to thereby reduce the amount of heat transferred from the leads to the microfluidic complex to an acceptable level (i.e., a level that does not significantly interfere with the operation of the microfluidic complex).

Other embodiments comprise combinations of the elements above that will be clear to those skilled in the art. For example, the vertical feed through, shown in FIGS. 5-7, can be combined with the thickened leads, (FIGS. 13-16), so that the leads 565 (see, e.g., FIG. 7) that are run "vertically" through the substrate 130 are increased in thickness, to further reduce heat emitted by the leads 565 and potentially transferred to the microfluidic complex 110. Similarly, the leads 560 (again, see FIG. 7) that run along the lower side of substrate 130 can also be increased in thickness to reduce heat emitted by the leads 560 that could be transmitted to the microfluidic complex 110, although preferably the substrate 130 is comprised of material with a thermal conductivity low enough to make such a modification unnecessary.

The amount of heat in a microfluidic complex may also be controlled using one or more Peltier devices. See FIGS. 8-12. Such devices can be made to act as heat pumps, removing unwanted heat from a microfluidic complex or component thereof. Peltier devices are well-known (see U.S. Pat. No. 5,714,701, to Chi et al., for example). Peltier discovered the effect that bears his name in 1834. Modem Peltier devices (also known as thermoelectric cooling devices) are typically composed of segments of heavily-doped semiconductors (often bismuth telluride) that are connected electrically in series and thermally in parallel between the heated and cooled surfaces of the device. Such devices are available commercially, for example, from MELCOR, 1040 Spruce Street, Trenton, N.J. 08648; see also http://www.melcor.com.

In this second preferred embodiment, at least one Peltier device 810 is attached to the substrate 130, although in an alternate embodiment at least one Peltier device 910 (see FIG. 9) is attached to the upper substrate 120 of a preferred microfluidic device. This "upper" Peltier device 910 can be in addition or an alternative to any "lower" Peltier devices 810 attached to the substrate 130. Preferred Peltier devices are battery-operated, and are attached to substrate 130 or substrate 120 using a heat-transfer paste, to improve heat conduction. In this embodiment, a Peltier device is used to cool an entire microfluidic chip. As discussed below, Peltier devices are used in other embodiments to cool selected areas of a chip, sometimes cooling different areas at different times, depending on the preferred operation of a microfluidic complex in the chip.

Figure 10:
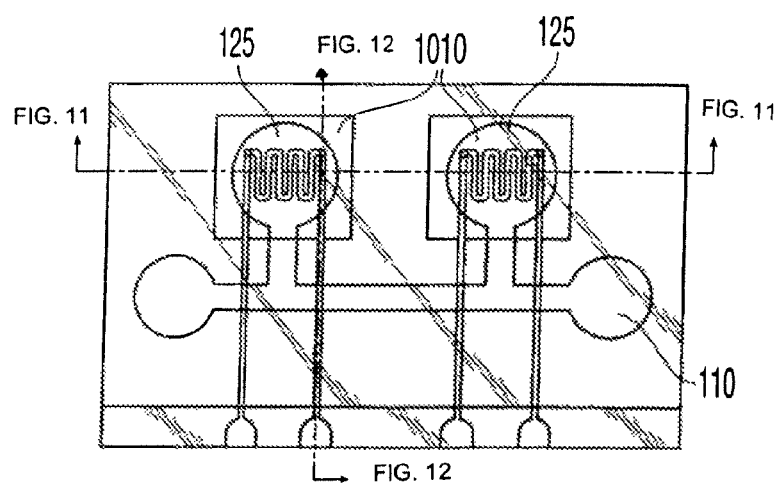
FIG. 10 depicts the device in FIG. 5, with multiple Peltier devices attached to the lower substrate.

Peltier devices are preferably used to remove heat primarily from selected areas of a microfluidic complex. For example, unnecessary power consumption would result if a Peltier device was cooling the entire substrate at the same time that a heater element was attempting to heat a selected chamber in the substrate. By using a plurality of Peltier devices, controlled electronically, heat can be removed from selected areas of a microfluidic complex while allowing other areas to be heated with a minimum of consumed power. FIG. 10 shows two Peltier devices 1010 attached to the bottom of substrate 130 so as to be capable of cooling selected areas (microchambers 125) of a microfluidic complex in substrate 120. The depicted configuration is, of course, merely exemplary—any operable configuration of multiple Peltier devices, where the Peltier devices are of any compatible collection of shapes, would also work in this embodiment. Further, although the depicted configuration is for a chip with heater leads as in FIGS. 5-7, a multiple-Peltier-device configuration can also be used on a microfluidic device such as that depicted in FIGS. 2-4. Multiple Peltier devices 910 can be similarly configured on the top substrate 120 of a microfluidic device. Peltier devices can be used to cool an entire microfluidic chip, an entire microfluidic complex, or selected portions (channels, chambers, etc.) thereof, and different Peltier devices can be used at different times, depending on desired functionality of the microfluidic complex.

Figure 11:
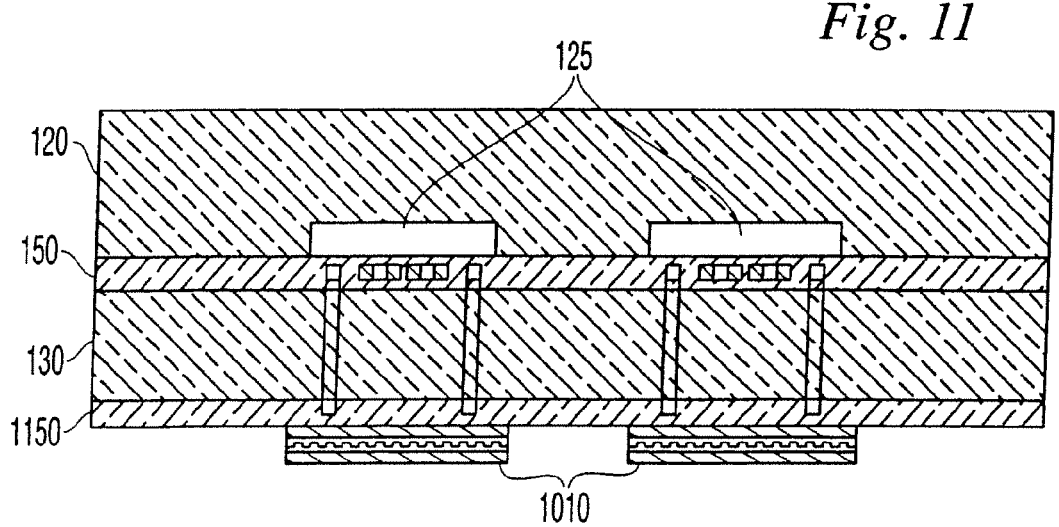
FIG. 11 depicts a cross-sectional end view of the device in FIG. 10.
Figure 12:
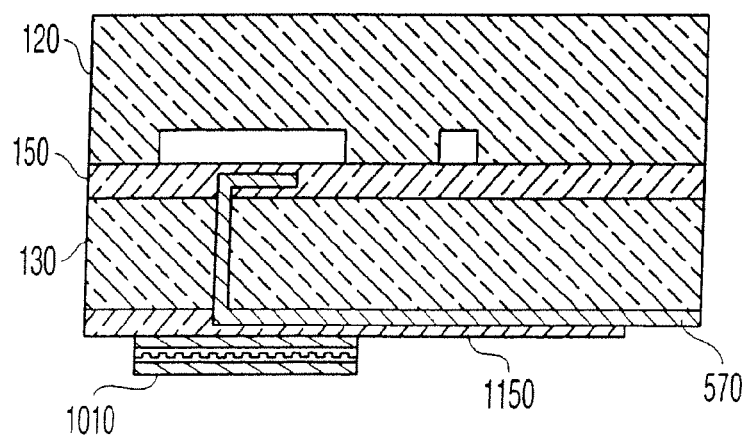
FIG. 12 depicts a cross-sectional side view of the device in FIG. 10.

FIGS. 11 and 12 depict cross-sectional views of the device in FIG. 10. A silicon oxide layer 1150 covers heater leads 560. A heat-transfer paste lies between silicon oxide layer 1150 and Peltier devices 1010.

While the operations described above have been for simple designs, the present invention contemplates more complicated devices involving the introduction of multiple samples and the movement of multiple microdroplets (including simultaneous movement of separate and discrete droplets), as well as multiple microchannels and microchambers, and potentially including meltable materials. Furthermore, as discussed above, those skilled in the art will recognize that the subject invention is not limited to microfluidic devices comprised of one glass substrate bound to another, or to microfluidic complexes formed by etching or otherwise forming chambers and channels into the bottom surface of an upper substrate that is then bonded to a lower substrate, or even to microfluidic devices formed by bonding one substrate to another. The present invention will be recognized by those skilled in the art as applying to any microfluidic device that comprises a microfluidic complex having a heating region.

Moreover, although much of the above description depicts, for simplicity of explanation, two leads running from each heater element, it is possible to share leads among heater elements so that, for example, two heater elements can be served by three leads (e.g., with the shared lead serving as a common ground).

What is claimed is:

1. An integrated microfluidic processing system comprising a microfluidic device, the device comprising:
   a first side;
   a second side;
   a microfluidic complex comprising a plurality of flow channels, wherein the microfluidic complex is located proximate to the first side of the microfluidic device and distant from the second side of the microfluidic device;
   a heating element configured to heat a region of the microfluidic complex, wherein the heating element is located relatively more distant from the first side of the microfluidic device and more proximate to the second side of the microfluidic device than the microfluidic complex; and
   at least one conductive lead for supplying electrical current from a current source to the heating element, wherein a portion of the lead extends from a first position within the microfluidic device that is similarly spaced with respect to the first and second sides of the microfluidic device as is the heating element to a second position within the microfluidic device located relatively more distant from the first side of the microfluidic device and more proximate to the second side of the microfluidic device than the heating element.

2. The integrated microfluidic processing system of claim 1, wherein the microfluidic device comprises a first substrate and a second substrate.

3. The integrated microfluidic processing system of claim 2, wherein the heating element is located in the second substrate.

4. The integrated microfluidic processing system of claim 2, wherein the microfluidic complex is defined in part by the first substrate.

5. The integrated microfluidic processing system of claim 2, wherein the microfluidic complex is located between the first and second substrates.

6. The integrated microfluidic processing system of claim 2, wherein the first and second substrate are in thermal communication.

7. The integrated microfluidic processing system of claim 2, wherein one of the flow channels in the microfluidic complex comprises a reaction chamber.

8. The integrated microfluidic processing system of claim 7, wherein the heating element is configured to heat the reaction chamber.

9. The integrated microfluidic processing system of claim 2, wherein the microfluidic complex comprises a valve.

10. The integrated microfluidic processing system of claim 9, wherein the valve is thermally actuatable.

11. The integrated microfluidic processing system of claim 9, wherein the heating element is configured to heat the valve.

12. The integrated microfluidic processing system of claim 1, further comprising a thermally isolating layer.

13. The integrated microfluidic processing system of claim 12, wherein the thermally is located between the first position of the lead and the second position of the lead.

14. The integrated microfluidic processing system of claim 13, wherein the lead passes through an opening in the thermally isolating layer.

15. An integrated microfluidic processing system comprising a microfluidic device, the microfluidic device comprising:
   a first side;
   a second side;
   a microfluidic complex comprising a plurality of flow channels, wherein the microfluidic complex is located proximate to the first side of the microfluidic device and distant from the second side of the microfluidic device;
   a heating element configured to heat a region of the microfluidic complex, wherein the heating element is located relatively more distant from the first side of the microfluidic device and more proximate to the second side of the microfluidic device than the microfluidic complex; and
   at least one conductive lead for supplying electrical current from a current source to the heating element, wherein the lead has a lower current density that the heating element.

16. The integrated microfluidic processing system of claim 15, wherein the heating element comprises a resistive material having a first cross-sectional dimension and a second cross-sectional dimension.

17. The integrated microfluidic processing system of claim 16, wherein the lead has a first crossOsectional dimension and a second cross-sectional dimension.

18. The integrated microfluidic processing system of claim 17, wherein the first cross-sectional dimension of the lead is larger than the first cross-sectional dimension of the heating element.

19. The integrated microfluidic processing system of claim 18, wherein the second cross-sectional dimension of the lead is larger than the second cross-sectional dimension of the heating element.

20. The integrated microfluidic processing system of claim 15, wherein the microfluidic device comprises a first substrate and a second substrate.

21. The integrated microfluidic processing system of claim 20, wherein the heating element is located in the second substrate.

22. The integrated microfluidic processing system of claim 20, wherein the microfluidic complex is defined in part by the first substrate.

23. The integrated microfluidic processing system of claim 20, wherein the microfluidic complex is located between the first and second substrates.

24. The integrated microfluidic processing system of claim 20, wherein the first and second substrate are in thermal communication.

25. The integrated microfluidic processing system of claim 20, wherein one of the flow channels in the microfluidic complex comprises a reaction chamber.

26. The integrated microfluidic processing system of claim 25, wherein the heating element is configured to heat the reaction chamber.

27. The integrated microfluidic processing system of claim 20, wherein the microfluidic complex comprises a valve.

28. The integrated microfluidic processing system of claim 27, wherein the valve is thermally actuatable.

29. The integrated microfluidic processing system of claim 27, wherein the heating element is configured to heat the valve.

* * * * *